United States Patent
Bennett et al.

[11] Patent Number: 5,873,847
[45] Date of Patent: Feb. 23, 1999

[54] ARTICULATED SPLINTS AND GONIOMETRIC HINGE FOR THE SAME

[75] Inventors: John Bennett, Rancho Palos Verdes; Willis C. Bradley, Gardena, both of Calif.

[73] Assignee: Lenjoy Engineering, Inc., Gardena, Calif.

[21] Appl. No.: 749,300

[22] Filed: Nov. 14, 1996

[51] Int. Cl.⁶ .................. A61F 5/00; E05F 1/14; E05C 17/64; F16C 11/00

[52] U.S. Cl. .................. 602/16; 602/20; 602/26; 403/116; 16/285; 16/342

[58] Field of Search .................. 602/5, 16, 20, 602/23, 24, 26; 601/23, 33, 34; 403/116, 117, 113; 16/285, 374, 342, 307; 482/124, 44, 127

[56] References Cited

U.S. PATENT DOCUMENTS

| | | | |
|---|---|---|---|
| 1,691,697 | 11/1928 | Bommer . | |
| 2,591,373 | 4/1952 | Petruch | 602/26 |
| 4,982,732 | 1/1991 | Morris | 602/16 |
| 5,052,379 | 10/1991 | Airy et al. | 602/26 |
| 5,109,570 | 5/1992 | Okada et al. | 16/289 |
| 5,123,768 | 6/1992 | Franklin | 403/96 |
| 5,131,385 | 7/1992 | Kuehnegger et al. | 602/26 X |
| 5,292,303 | 3/1994 | Bastyr et al. | 602/26 X |
| 5,334,354 | 8/1994 | Johnston et al. | 16/307 X |
| 5,358,469 | 10/1994 | Patchel et al. | 602/26 X |
| 5,460,599 | 10/1995 | Davis et al. | 602/26 |
| 5,462,517 | 10/1995 | Mann | 602/26 |
| 5,472,410 | 12/1995 | Hamersly | 602/16 |
| 5,632,725 | 5/1997 | Silver et al. | 602/26 |

*Primary Examiner*—Linda C. Dvorak
*Attorney, Agent, or Firm*—Natan Epstein

[57] ABSTRACT

An orthopedic splint has two end plates connected to an intermediate hinge which flexes in a plane transverse to the plates and attaches to a limb in a less obtrusive position behind the joint rather than on opposite sides of the joint. The hinge has continuously adjustable stops for limiting flexing and extension and a spring contained in the hinge for preloading the splint. The entire splint including the hinge may be enclosed and contained in a zippered moisture absorbent contour fitting cover for improved esthetic appearance and comfort.

47 Claims, 3 Drawing Sheets

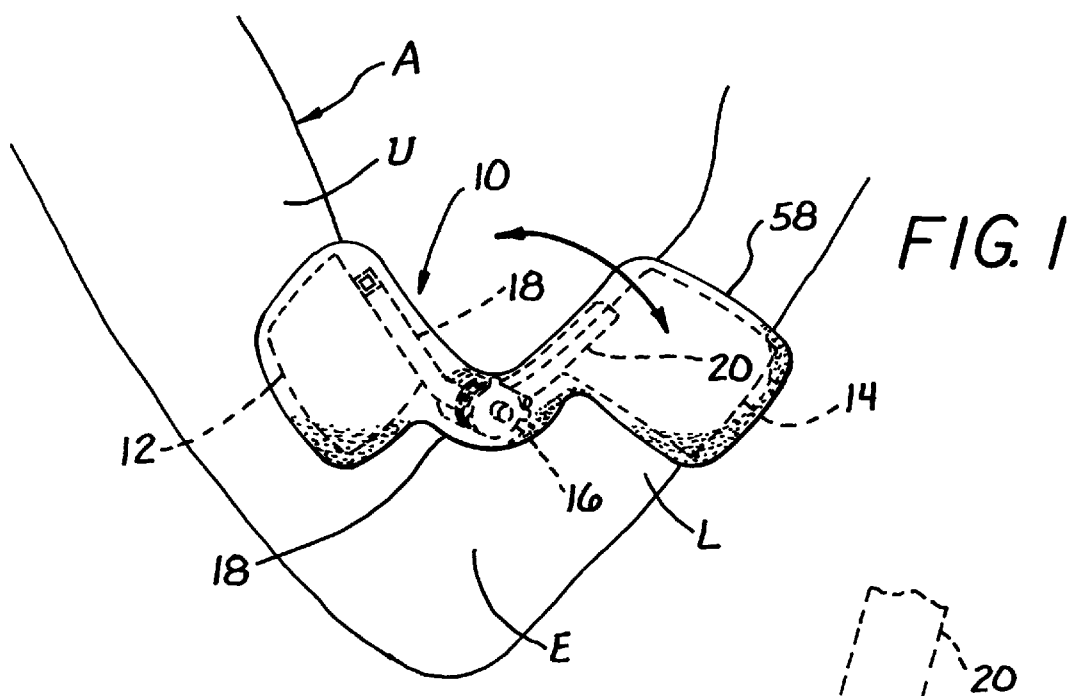
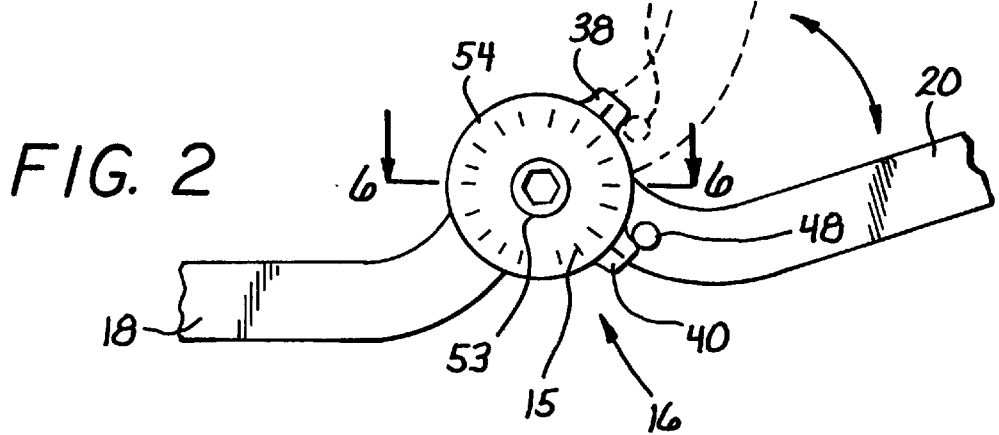
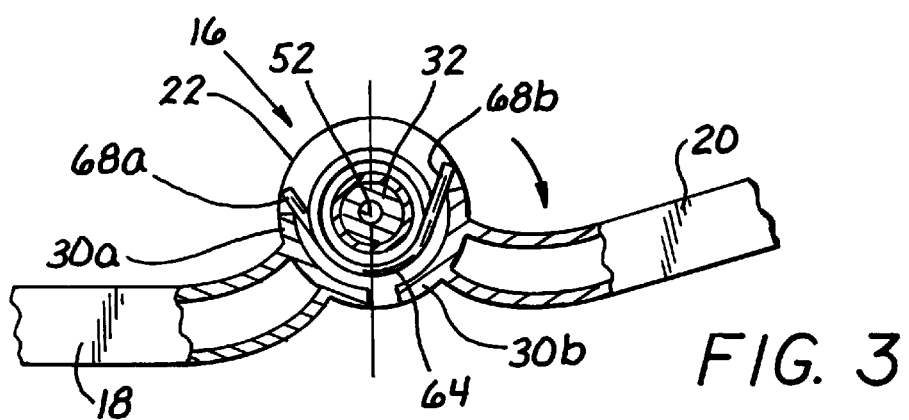

ARTICULATED SPLINTS AND GONIOMETRIC HINGE FOR THE SAME

BACKGROUND OF THE INVENTION

1. Field of the Invention

This invention pertains to the field of orthopedic splints and orthoses, and more particularly concerns articulated splints used in physical therapy designed to improve extension of a limb.

2. State of the Prior Art

Orthotic splints are used to assist extension of a joint, typically the knee, elbow or wrist, of a patient for therapeutic reasons. Such splints are well known and commonly used in physical therapy designed to reverse the involuntary contraction of muscles which typically results from protracted disuse of the muscles. This neuromuscular condition is frequent in disabled or comatose patients who are bedridden for long periods of time. The arm, leg and finger muscles become contracted, causing permanent retraction of the elbow, wrist or knee joints. Such a condition can be reversed with physical therapy, by gradually forcing the joints towards an extended condition in small daily increments. After each such extension the involved limb is held at the newly achieved degree of extension by a splint which is attached to the limb and bridges the affected joint. After a number of such sessions the limb may regain a normal range of motion. Splints are also employed in the treatment of other conditions where mobility of a diseased or injured joint must be restricted for therapeutic reasons.

Such splints generally have two end portions, which are fastened to opposite sides of the joint in question by means of straps. The end portions are usually plates curved to fit against the limb surface, and are joined by an intermediate portion which is pliable or flexible to allow bending of the splint to fit the angle of the joint. In its simplest form, a splint has two end plates joined by a narrower midportion which is sufficiently rigid so that the patient is not able to change its shape, yet sufficiently deformable that the therapist can bend it to a desired angle. The splint requires successive adjustment as limb extension progresses, which is also accomplished by bending the semi-rigid intermediate portion of the splint. This simple type of splint merely immobilizes the joint to prevent retraction of the limb.

For some patients, however, it is desirable to allow a limited range of motion of the joint, which may be gradually adjusted and increased as therapy progresses. For this purpose, articulated splints are available which are equipped with a specialized hinge, known as a goniometer. The goniometer has adjustable stops which can be preset by the physical therapist to allow a limited range of motion appropriate to the particular patients needs and condition. in some cases it may be also beneficial to provide a continuous force, as by a spring, urging the limb towards an extended condition to compensate for the greater natural strength of the retractor muscles as compared with extensor muscles and thereby assist the patient in extension of the limb.

Existing articulated splints are of cumbersome design in that the goniometer hinge is in the form of two spaced apart pivots positioned on opposite sides of the joint when the splint is applied to the patient's limb. Range of motion settings must be made on each of the two sides of the goniometer hinge by the therapist. Existing splint goniometers suffer from the additional shortcoming that the range of motion settings are not continuously adjustable, as would be desirable, but only in discrete steps by means of stop pins inserted in a limited number of holes spaced along an arc on the goniometer hinge. Still further, the goniometer hinge on existing splints remains exposed to view on the patient's limb and makes for an awkward looking, aesthetically unappealing apparatus.

What is needed is a splint with a goniometer hinge arrangement which is more compact, easier to adjust, has a continuous range of adjustment, and is less conspicuous when worn by the patient.

SUMMARY OF THE INVENTION

This invention provides a splint for bridging a joint on a human limb having first and second end portions for attachment to corresponding limb sections on opposite sides of the joint, and a hinge connecting the end portions along a center line of the end portions. The splint places the hinge substantially against the inside of the joint, that is, against the inside of the knee or elbow for example, when the end portions of the splint are correctly attached to the leg or arm. The hinge is compact and generally small in relation to the end portions. The end portions each have a width dimension and the hinge has an axial dimension substantially smaller than the width dimension of either of the end portions. The hinge is connected to each end portion by a single corresponding shank at an intermediate location along the width dimension of the end portions.

The end portions may be first and second generally rectangular end plates adapted to conform to a limb, each of the end plates being connected by a respective shank to a single hinge. The shank of each of the end plates may lie substantially along a common line approximately bisecting the end plates. The end plates may be, for example, of relatively soft steel sheeting, formable to a shape conforming to a limb to which said splint is to be attached.

The end plates joined by the hinge form a framework which is contained in a covering adapted to fit over and enclose the end portions and the hinge. The covering may be a unitary covering of moisture absorbent material such as terry cloth, fitted over the end portions and the hinge, such that the hinge is substantially or entirely hidden from view by the cloth covering. The covering may have a zippered opening for receiving the framework, and it is preferable that the covering be removable for washing.

In its presently preferred form, the hinge has first and second stops for limiting flexing of the splint between an extended and a retracted position, and one or both of the stops are continuously adjustable for setting a selectable range of movement between the extended and retracted positions. In one form of the invention, the hinge is spring biased towards its extended condition.

The hinge may include first and second swivels, each swivel supporting one of the end plates, a shaft through the swivels defining a hinge axis, and stop elements individually positionable about the hinge axis. One of the swivels may be fixed to the shaft, and a detent such as a stop pin may be affixed to the other swivel, such that the stops engage the detent at selected extended and retracted positions for limiting rotation of the swivels relative to each other. The swivels each have axially extending portions, such as cylindrically curved plate portions curved coaxially to the hinge axis, and each of the end plates is connected to the axially extending plate portions as by a corresponding rigid shank.

The adjustable stops may comprise a pair of stop rings each having a stop tab thereon, the stop rings being mounted for rotation about the hinge axis, and a lock such as a friction lock engageable for fixing the stop rings with the stop tabs at selected angular positions relative to each other about the hinge axis. The friction lock may include a backing plate mounted to the shaft, a pressure plate, and a threaded bolt for adjustably urging the pressure plate against the backing plate. The pressure plate and the backing plate may have interlocking portions preventing rotation of the pressure plate about the hinge axis to capture the stop rings between the backing plate and the pressure plate. Indicia representative of the angular position of the stop tabs may be provided at a convenient location on the hinge.

The biasing spring may be a coil spring mounted radially inwardly of the plate portions of the hinge, the spring having end tangs engaged to the plate portions for biasing the swivels to either the retracted or the extended position.

The present invention contemplates the use of the adjustable hinge for applications other than orthopedic splints, and consequently the hinge without the end portions attached thereto is considered a novel aspect of this invention. Other structures may be hinged to each other by attaching the structures respectively to the two swivels of the hinge, in particular, to the plate portion of each swivel in lieu of the shanks attached to these portions.

BRIEF DESCRIPTION OF THE DRAWINGS

FIG. 1 is a perspective view showing an articulated elbow splint according to this invention applied to the arm of a patient;

FIG. 2 is a side view of the hinge in the splint of FIG. 1, illustrating the range of motion of the splint between the solid lined extended position and phantom lined retracted position;

FIG. 3 is a side view of the hinge broken away to show its interior;

DETAILED DESCRIPTION OF THE PREFERRED EMBODIMENTS

Figure 4:
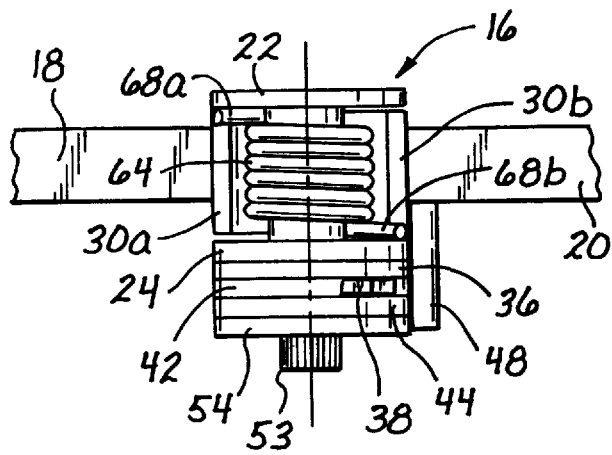
FIG. 4 is a top view of the hinge of FIG. 2.

With reference to the accompanying drawings in which like elements are designated by like numerals, FIG. 1 shows an orthotic elbow splint 10 attached to the arm A of a patient. The splint 10 has end portions 12, 14 which are respectively fastened to the upper arm U and lower arm L so as to bridge the elbow joint E of the patient's arm A. The end portions 12, 14 are joined by a splint hinge 16, as will be described in greater detail below, to make up an interior framework indicated in phantom lining in FIG. 1 which is covered by and contained in an exterior cover 18 shown in solid lining in the same Figure.

The end portions 12, 14 are generally rectangular plates of a semi-rigid, deformable material such as a soft steel. The end plates may be flat or planar in an initial condition of the splint and can be bent and shaped by a physical therapist to fit the surface curvature of a given limb such as arm A. Each end plate 12, 14 is welded to an outer end of a corresponding shank 18, 20. The two shanks are made of generally rigid tubular steel of rectangular cross-section.

Figure 5:
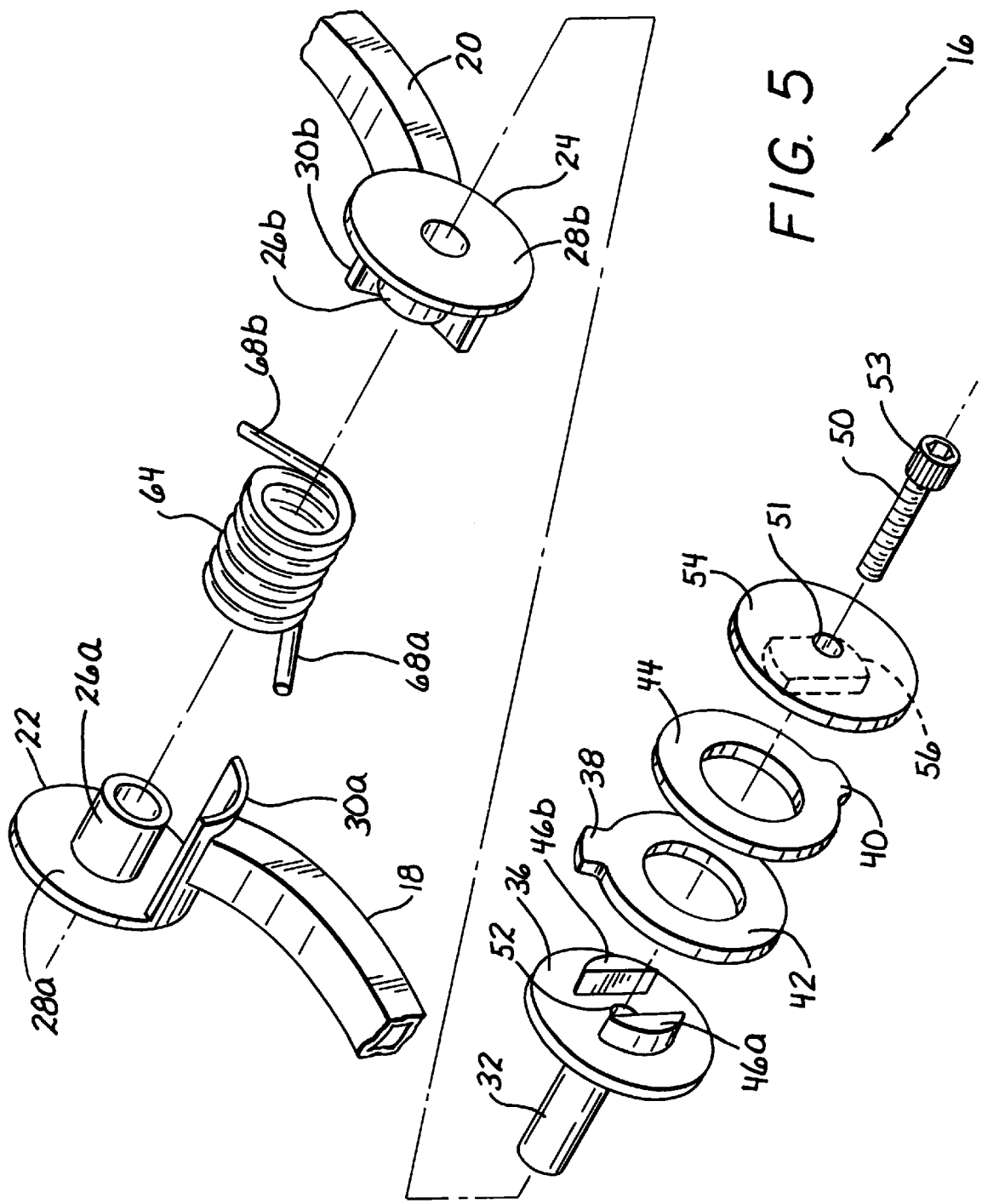
FIG. 5 is an exploded perspective of the hinge of FIG. 2.

The construction of the splint hinge 16 is shown in detail in FIGS. 2 through 6 of the drawings. As best seen in FIG. 5, the hinge has two swivels 22, 24. Each swivel has a short tubular segment 26a, 26b which extends axially from an end disk 28a, 28b. Each swivel also has a cylindrically curved plate portion 30a, 30b which extends axially from the end plate in coaxial relationship with the tubular segment of the swivel, as best understood by reference to the axial view in FIG. 3.

Figure 6:
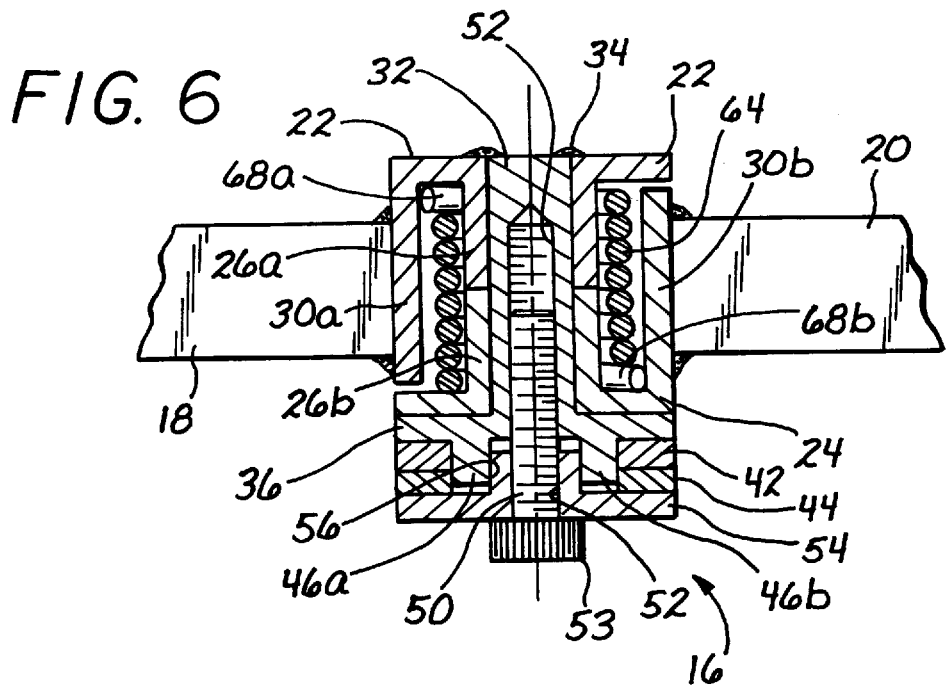
FIG. 6 is a longitudinal section of the hinge taken along line 6—6 in FIG. 2.

The two swivels 22, 24 are supported on a common shaft 32 inserted through the axially aligned tubular segments 26 of the swivels, as best shown in FIG. 6. Swivel 22 is welded to the shaft 32 at 34, while the other swivel 24 is axially captive between the fixed swivel 22 and a backing plate 36 fixed to the end of shaft 32, and is free to turn about shaft 32.

The inner end of each shank 18, 20 is welded to the plate portion 30a, 30b of a corresponding one of the two swivel elements 22, 24 of the hinge 16, as best seen in FIG. 3. The angle measured between the two shanks 18, 20 about shaft 32 can be changed in a continuous manner, by turning swivel 24 relative to swivel 22 on the shaft, between a maximal extended position and a maximal retracted position defined by contact between the arcuate plate portions 30a, 30b at these positions. At the maximal extended position the two shanks form an angle of approximately 180 degrees, as generally illustrated in FIG. 3 and in solid lining in FIG. 2. At the maximal retracted position, not illustrated in the drawings, the shanks are folded together with approximately a zero degree angle between them. For therapeutic purposes, the range of angular displacement between the two shanks can be limited to any arbitrary arc segment contained between the maximal extended and retracted positions. For this purpose adjustable stops in the form of stop tabs 38, 40 are provided on corresponding rings 42, 44 each of which turns freely about a pivot defined by two disc segments 46a, 46b on backing plate 36. Each of the two rings 42, 44 can be adjusted to position the two stop tabs 38, 40 at an arbitrary angle with respect to each other. A stop pin 48 fixed to the shank 20 extends axially alongside the hinge axis between the two stop tabs, so that the angle of possible arcuate movement of the shank 20, and consequently of the end plate 14 relative to the end plate 12, is determined by the angular spacing and positioning of the two stop tabs 38, 40. For this purpose, graduation lines 15 or similar indicia may be inscribed or applied to the pressure plate 54, as indicated in FIG. 2. As depicted in FIG. 2, clockwise movement of the stop pin 48 during extension of the splint is limited by stop tab 40, while retraction of the splint by counterclockwise movement of the shank 20 is limited by contact of the stop pin 48 with the other stop tab 38.

The splint 10 can be locked in a particular angular relationship of the two end plates 12, 14 by bringing the stop tabs against opposite sides of the stop pin 48. Maximum angular movement of the splint is achieved by positioning the stop tabs 38, 40 apart from each other so that pivotal movement of shank 20 is limited only at the maximal extended and retracted positions of the hinge by the plate portions 30a, 30b, as earlier explained.

A friction lock for securing the stop tabs in a desired position is provided by turning bolt 50 in a threaded bore 52 which is centered axially in the shaft 32, as seen in FIG. 6. The bolt 50 passes through a center hole 51 in a pressure plate 54 and the head 53 of the bolt 50 bears against pressure plate 54, which in turn presses the two rings 42, 44 against backing plate 36. The pressure plate 54 is fixed against rotation by a key 56 which projects axially and fits between the disc segments 46a, 46b through the center openings in the rings 42, 44, so that by sufficiently tightening the bolt 50 the rings can be held against rotation between the pressure plate 54 and backing plate 36 by frictional clamping force developed in the axial direction of bolt 50.

Figure 7:
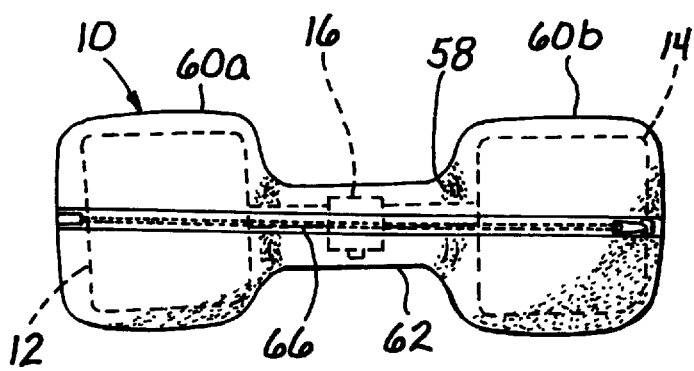
FIG. 7 is a bottom plan view of the splint of FIG. 1, showing the zippered access opening of the splint cover.

Seen in top or bottom plan view, as in the bottom view of FIG. 7, the two shanks 18, 20 are in line with each other and radial to the axis of hinge 16, and are welded to a midline of the respective end plates 12, 14, generally bisecting the respective end plates. It will be appreciated that the hinge 16 is compact and relatively small in relation to the dimensions of the end plates, and in particular the hinge 16 is much smaller in its axial direction than the width of the end plates in the same direction. Because of these dimensions and arrangement, the hinge 16 lies close to the inside of the joint, e.g. elbow wrist or knee, as the case may be, of the limb to which the splint 10 is applied. In the illustrated example of FIG. 1, the hinge 16 lies close to the inside of the elbow E, which makes the hinge relatively unobtrusive and inconspicuous, even to the patient wearing the splint.

The splint inner framework described above is covered with an outer covering 58 which contains and completely envelops all parts of the metallic framework, as shown in FIGS. 1 and 7. The presently preferred covering 58 is made of moisture absorbent material such as terry cloth, sewn into a unitary cover with pockets 60a, 60b at opposite ends for receiving the end plates 12, 14 and a narrower intermediate portion 62 which covers the shanks 18, 20 and hinge 16. The cover 58 has a zippered longitudinal slit 66, seen in FIG. 7, on one side for access to the interior of the covering. The covering 58 hides the hinge 16 from view and prevents skin-to-metal contact by the user, makes the splint 10 more comfortable and far less objectionable from an esthetic point of view than other currently known splints with goniometric hinges.

The splint 10 may be optionally equipped with a coil spring 64 for providing a continuous bias urging the splint towards an extended condition. This is desirable in cases where the therapist wishes to increase the extension range of a patient's limb. The spring bias supplements the force of the limb's extensor muscles which are normally considerably weaker than the retractor muscles of the same limb, and encourages extension of the limb by the patient. Spring 64 is wound about the two tubular segments 26 of the swivels 22, 24, in radially interior relationship to the plate portions 30a, 30b, and has two end tangs 68a, 68b which extend tangentially away from the tubular segments 26. The free end of each end tang extends radially outwardly into circumferential engagement with a corresponding one of the plate portions 30a, 30b of the two swivels as shown in FIGS. 3 and 4, continuously urging the swivels towards the extended condition of the hinge shown in solid lining in FIG. 2. The coil spring is provided only where appropriate for the therapeutic benefit of the user, and may be otherwise omitted from the splint 10 without need for other modification to the hinge 16 or the splint. The coil spring can be reversed on the shaft 32 to engage the circumferentially opposite edge of each plate portion and thus bias the hinge in the opposite direction, i.e. towards retraction, as may be appropriate for a particular patient.

The articulated splint of this invention can be readily adapted for use on any joint of the human body by suitable choice of the end plates to fit the contour of the affected limb or anatomy, including fingers, wrist, ankle and neck, and nothing herein is intended to restrict its use to any particular limbs or joints.

Furthermore, the adjustable hinge disclosed herein may find many applications other than in the splints described above, for example in any devices where hinging motion is to be restricted within adjustable limits, so that the novelty of the hinge is not to be limited to any particular application.

While a preferred embodiment of the invention has been shown and illustrated for purposes of clarity and explanation it should be understood that many changes, modifications and substitutions to the described embodiment will be readily apparent to those having ordinary skill in the art without thereby departing from the scope and spirit of the invention defined in the following claims.

What is claimed as new is:

1. A splint for bridging a joint on a human limb, comprising:
    first and second end plates shaped and configured for attachment to corresponding limb sections on opposite sides of a said joint; and
    a hinge connecting said end portions along a center line of said end plates, said hinge flexing in a plane generally transverse to said end plates at said center line.

2. The splint of claim 1 wherein said end plates are deformable from an initially planar condition to a curved limb conforming condition for said attachment.

3. The splint of claim 1 wherein said end plates each have a width dimension and said hinge has an axial dimension substantially smaller than said width dimension of either of said end plates.

4. The splint of claim 3 wherein said hinge is generally centered along said width dimension of each of said end plates.

5. The splint of claim 1 wherein said axial dimension is generally small in relation to said width dimension.

6. The splint of claim 1 wherein each of said end plates is connected to said hinge by a single corresponding shank.

7. The splint of claim 1 further comprising a cloth covering fitted over said end plates and said hinge, such that said hinge is substantially hidden from view by said cloth covering.

8. The splint of claim 7 wherein said cloth covering is a unitary removable covering.

9. The splint of claim 1 wherein said hinge has first and second stops for limiting said flexing between an extended and a retracted position of said splint, characterized in that one or both of said stops are continuously adjustable for setting a range of movement between said extended and said retracted conditions.

10. The splint of claim 9 wherein said hinge is spring biased towards said extended condition.

11. A splint for bridging a joint of a human limb, comprising:
    an inner framework having first and second end plates adapted to conform to said limb, each of said end plates connected by a respective shank to a hinge flexible in a plane generally transverse to said end plates; and
    a unitary cloth covering having end portions contoured to conform to each of said end plates and a narrower midportion adapted to fit over and enclose said shanks and said hinge, such that said inner framework is substantially entirely enveloped by said unitary cloth covering.

12. The splint of claim 11 wherein said respective shank of each of said end plates lies substantially along a common line approximately bisecting said end plates.

13. The splint of claim 12 wherein said cloth covering has a zippered opening for receiving said inner framework.

14. The splint of claim 12 wherein said hinge has first and second stops for limiting said flexing between an extended and a retracted position of said splint, characterized in that one or both of said stops are continuously adjustable for setting a range of movement between said extended and said retracted conditions.

15. The splint of claim 14 wherein said hinge is spring biased towards said extended condition.

16. A splint for attachment to a joint of a human limb comprising first and second end plates connected to each other by a hinge to allow flexing of the splint about a hinge axis, said hinge having first and second stops for limiting said flexing between an extended and a retracted position of said splint, characterized in that one or both of said stops are continuously rotatable about said hinge axis for setting a limited range of movement of any arbitrary arc segment contained between said extended and said retracted conditions.

17. The splint of claim 16 wherein said hinge is spring biased towards said extended condition.

18. The splint of claim 16 further comprising a spring normally urging said hinge towards said extended condition.

19. The splint of claim 18 wherein said spring is a coil spring supported about said shaft and both axially and radially contained between said swivels.

20. The splint of claim 19 wherein said swivels each have a side portion and a plate portion, the plate portions extending axially between the side portions, said coil spring being axially contained between the side portions and radially contained between the plate portions.

21. The splint of claim 20 wherein said axially extending portions are cylindrically curved plate portions generally coaxially to said shaft and together defining a generally cylindrical enclosure about said coil spring.

22. The splint of claim 20 wherein said spring has end tangs engaged to the plate portions for biasing said swivels to said extended condition.

23. The splint of claim 16 wherein said hinge comprises first and second swivels, each of said end plates supported on a corresponding one of said swivels, a shaft through said swivels along said hinge axis, bolt means threaded along said hinge axis, each of said stops comprising a disk shaped stop element individually rotatable about said shaft, each said stop element being held against rotation relative to a first one of said swivels in a tightened condition of said bolt means.

24. The splint of claim 23 wherein one of said end plates is fixedly attached to said first one of said swivels, further comprising a detent affixed for movement with the other one of said swivels, said stops engaging said detent at said extended and retracted positions for limiting rotation of said swivels relative to each other.

25. The splint of claim 23 wherein each said end plate is attached to a said plate portion on a said corresponding one of said swivels by means of a rigid shank.

26. The splint of claim 16 wherein said end plates each comprise a plate formable to a shape conforming to a limb to which said splint is to be attached.

27. The splint of claim 26 wherein said plate is of relatively soft steel sheeting.

28. The splint of claim 16 further comprising a covering substantially enveloping said splint including said hinge, said covering being of a moisture absorbent material.

29. The splint of claim 28 wherein said moisture absorbent material is a terry cloth fabric.

30. The splint of claim 16 wherein said stops comprise a pair of stop plates each having a stop thereon, said plates mounted for rotation about said hinge axis independently of one another, and lock means engageable for fixing said plates with said stops at selected angular positions relative to each other about said hinge axis, said lock means comprising a threaded bolt through said hinge axis, said plates being frictionally held against rotation in a tightened condition of said bolt.

31. The splint of claim 16 wherein each of said end plates is fixed to a corresponding one of two swivels and further comprising a shaft passing axially through said swivels, friction lock means comprising a backing plate mounted to said shaft, a pressure plate, and threaded means for adjustably urging said pressure plate against said backing plate, said stop plates being captive between said backing plate and said pressure plate.

32. The splint of claim 31 wherein said threaded means is a bolt in a threaded bore axially centered in said shaft.

33. The splint of claim 31 wherein said pressure plate and said backing plate have interlocking means preventing rotation of said pressure plate about said hinge axis.

34. The splint of claim 33 wherein said interlocking means engage each other through center openings defined in said stop plates.

35. A splint for bridging a joint of a human limb, comprising:
   an inner framework having first and second end plates deformable to conform to a said limb, each of said end plates connected by a rigid shank to a single hinge;
   said hinge having two swivels each connected to a respective said shank, said swivels together defining a generally cylindrical enclosure axially and radially containing a spring operative for biasing the splint towards an extended condition;
   first and second stops on said hinge continuously adjustable for setting a limited range of movement of any arbitrary arc contained between an extended and a retracted condition of said end plates; and
   a moisture absorbent covering adapted to fit over and enclose said inner framework including said hinge.

36. The splint of claim 35 wherein said shank of each said plate lies with said hinge approximately along a common line generally bisecting said plates.

37. The splint of claim 25 wherein said cloth covering has an opening for receiving said inner framework and a fastener for closing said opening.

38. A hinge comprising first and second swivels, a shaft through said swivels defining a hinge axis, a detent element supported to one of said swivels,
   a pair of stop plates each having a stop thereon, said plates mounted for continuous rotation about said hinge axis, and friction lock means threaded to said swivels axially along said hinge axis and engageable for fixing said plates with said stops at selected angular positions relative to each other about said hinge axis;
   said stops cooperating with said detent element for limiting rotation of said swivels between a maximally extended and a maximally retracted position of said hinge within a continuously adjustable arbitrary arc of movement contained between said maximally extended and said maximally retracted conditions.

39. The hinge of claim 38 further comprising a spring supported about said shaft and both axially and radially contained between said swivels for biasing said swivels towards either an extended or a retracted position.

40. The splint of claim 39 wherein said swivels each have axially extending portions for supporting first and second structures in hinged relationship to one another.

41. The splint of claim 40 wherein said axially extending portions are cylindrically curved plate portions.

42. The splint of claim 41 wherein said cylindrically curved plate portions are curved coaxially to said hinge axis.

43. The splint of claim 38 further comprising a coil spring supported about said shaft for biasing said swivels towards either an extended or a retracted position, wherein said plate portions extend radially outwardly to said spring, and said spring has end tangs engaged to said plate portions for said biasing said swivels.

44. The splint of claim 38 wherein said friction lock means comprise a backing plate mounted to said shaft, a pressure plate, said friction lock means operative for adjustably urging said pressure plate against said backing plate, said stop plates being captive between said backing plate and said pressure plate.

45. The splint of claim 44 wherein said threaded means is a bolt in a threaded bore axially centered in said shaft.

46. The splint of claim 45 wherein said pressure plate and said backing plate have interlocking means preventing rotation of said pressure plate about said hinge axis.

47. The splint of claim 46 wherein said interlocking means engage each other through center openings defined in said stop plates.

* * * * *